(12) United States Patent
Aboff

(10) Patent No.: US 7,837,649 B1
(45) Date of Patent: Nov. 23, 2010

(54) NASAL CLIP FOR AROMATIC SUBSTANCES

(76) Inventor: Clifford S. Aboff, 770 Hartwell St., Teaneck, NJ (US) 07666

( * ) Notice: Subject to any disclaimer, the term of this patent is extended or adjusted under 35 U.S.C. 154(b) by 1354 days.

(21) Appl. No.: 11/268,104

(22) Filed: Nov. 7, 2005

(51) Int. Cl.
*A61M 11/00* (2006.01)
*A61M 51/08* (2006.01)

(52) U.S. Cl. ............... 604/93; 424/442; 424/94; 424/77; 424/23; 604/94; 604/77; 604/23; 604/304; 128/204

(58) Field of Classification Search ........... 604/93, 604/94, 77; 424/442
See application file for complete search history.

(56) References Cited

U.S. PATENT DOCUMENTS

| | | | |
|---|---|---|---|
| 3,828,577 A * | 8/1974 | Haynes | 63/33 |
| 4,220,150 A | 9/1980 | King | |
| 4,221,217 A | 9/1980 | Amezcua | |
| 5,479,944 A | 1/1996 | Petruson | |
| 5,706,800 A | 1/1998 | Cronk et al. | |
| 6,645,172 B1 * | 11/2003 | Gueret | 604/93.01 |
| 6,769,428 B2 | 8/2004 | Cronk et al. | |

FOREIGN PATENT DOCUMENTS

DE    29816141 U1 *    3/1999

* cited by examiner

*Primary Examiner*—Ardin Marschel
*Assistant Examiner*—Zohreh Vakili
(74) *Attorney, Agent, or Firm*—Law Offices of Mitchell P. Novick

(57) ABSTRACT

The present invention provides a nasal clip including two parts which are both injection molded. The first part, the base with a holster cavity for the second piece, the scent bar, which is impregnated with an aromatic substance such as essential oils, or aromatic medications. The purpose of the holster cavity is to keep the scent bar away from the skin, since the oils can irritate the skin if in direct contact. The base is fashioned in a way with various openings in order to emit as much aroma as possible. The scent bar is formed of a porous material, such as a poly-olefin plastic that undergoes a process of impregnation on saturation with the aromatic substance. The concentration of each type of aromatic substance will determine the length of time the scent bar will be soaked with may range from as little as a few hours to as much as a week. The nature of the poly-olefin plastic is to naturally absorb up to 30% of the aromatic substance.

14 Claims, 2 Drawing Sheets

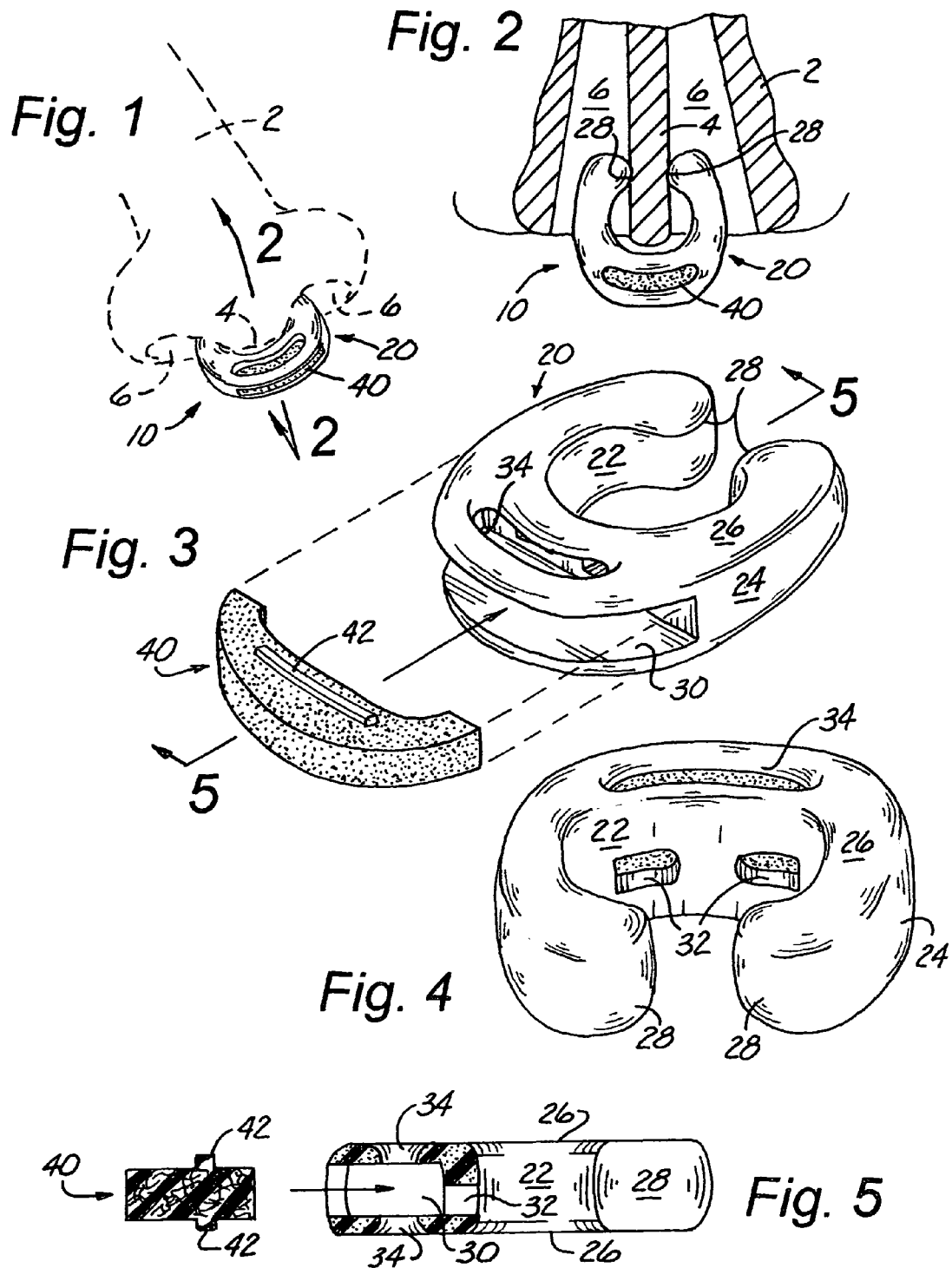

NASAL CLIP FOR AROMATIC SUBSTANCES

BACKGROUND OF THE INVENTION

1. Field of the Invention

The present invention relates to the field of nasal clips, and more particularly to a nasal clip that effuses the scent of aromatic substances for aroma therapy uses.

2. Description of Related Art

Various aromas and medications improve smell and give relief from nausea or queasiness in people such as pregnant women with morning sickness, people undergoing chemotherapy, or HIV treatments, people with colds and allergies, people prone to motion sickness, people exposed to noxious odors, people with hyper-sensitive smell, and others.

Aroma therapy is the practice of using volatile plant oils or essential oils for psychological and physical well being. Essential oils are the pure essence of a plant that is generally distilled from leaves, stems, flowers, bark, roots, or other elements of a plant. It is believed that the aroma of the natural essential oil stimulates the brain to trigger a reaction. Aroma therapy will not cure serious illnesses such as cancer or aids, however, it can help enhance a patient's quality of life by enhancing the patient's mood, as well as easing nausea. Aroma therapy is practiced through diffusing oils in various methods. There are many diffusers out on the market today. Examples are steamers, candles, clay pots, lamp rings, etc. All of these products have one disadvantage in common. They diffuse the scent of the oil into a room or area in a manner that effects everyone in the vicinity.

As a consequence of the foregoing situation, there has existed a longstanding need among for a new and improved device for practicing aroma therapy, and the provision of such a device is a stated objective of the present invention.

BRIEF SUMMARY OF THE INVENTION

Briefly stated, the present invention provides a nasal clip including two parts which are both injection molded. The first part, the base with a holster cavity for the second piece, the scent bar, which is impregnated with an aromatic substance such as essential oils, or aromatic medications. The purpose of the holster cavity is to keep the scent bar away from the skin, since the oils can irritate the skin if in direct contact. The base is fashioned in a way with various openings in order to emit as much aroma as possible. The scent bar is formed of a porous material, such as a poly-olefin plastic that undergoes a process of impregnation on saturation with the aromatic substance. The concentration of each type of aromatic substance will determine the length of time the scent bar will be soaked which may range from as little as a few hours to as much as a week. The nature of the poly-olefin plastic is to naturally absorb up to 30% of the aromatic substance.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 1 is a perspective view showing the nasal clip of the present invention disposed to engage the nasal septum of the user;

FIG. 2 is a sectional view taken along line 2-2 of FIG. 1;

FIG. 3 is an enlarged exploded perspective view illustrating the scent bar being inserted into the holster cavity on the lower portion of the base;

FIG. 4 is a perspective view from the top of the nasal clip with the scent bar inserted in the holster cavity showing the openings in the proximal edge of the base that allow the scent from the scent bar to diffuse directed up into the user's nasal passages;

FIG. 5 is a sectional view taken along line 5-5 of FIG. 3;

DETAILED DESCRIPTION OF THE INVENTION

Figure 6:
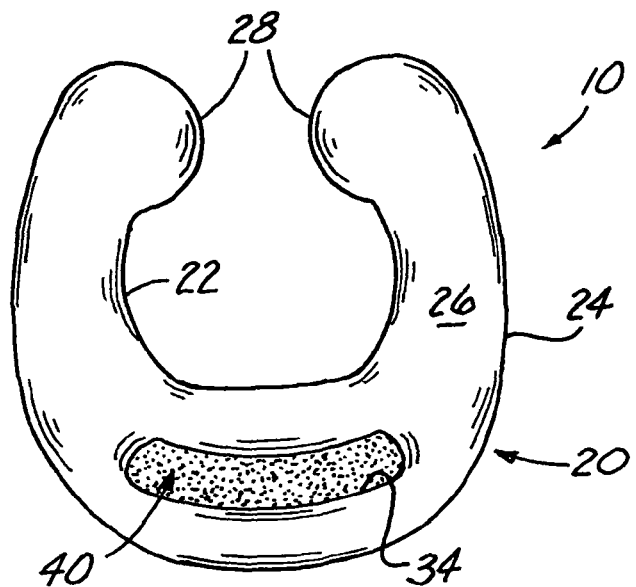
FIG. 6 is a front elevational view of the nasal clip with the scent bar inserted.
Figure 7:
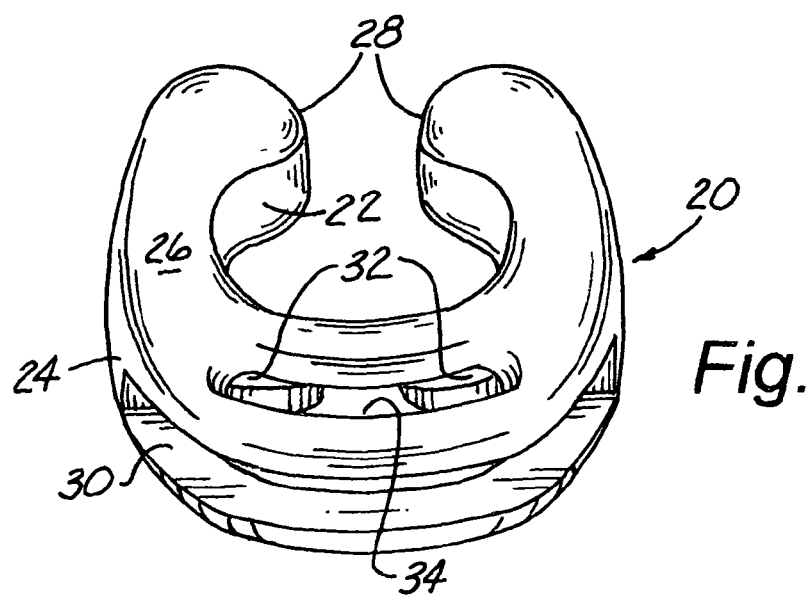
FIG. 7 is a perspective view of the base of the nasal clip with the scent bar removed.

As can be seen by reference to the drawings, and in particular to FIG. 1, the nasal clip that forms the basis of the present invention is designated generally by the reference number 10. The clip 10 is shown engaging the nose 2 of the user by grippingly engaging the septum 4 between the nasal passages 6. As most clearly shown in FIGS. 3 and 5, the nasal clip 10 includes a U-shaped base 20 and a scent bar 40.

The U-shaped base 20 has a proximal edge 22, a distal edge 24, interior and exterior faces 26, and a pair of free ends 28 that are biased toward each other to grip the septum 4 of the user. The lower portion of the base 20 remote from the free ends 28 has a holster cavity 30 formed therein. Openings 32 communicate between the holster cavity 30 and the proximal edge 22, and openings 34 communicate between the holster cavity and the interior and exterior faces 26. The base 20 may be made of any suitable material such as injection molded plastics that are flexible and have memory.

The scent bar 40 is shaped to be matingly received in the holster cavity 30 of the base 20, and includes ridges 42 that frictionally engage or snap fit into the openings 34 in the holster cavity 30. The scent bar 40 is impregnated or saturated with an aromatic substance such as an essential oil or an aromatic medication. The scent bar is soaked in the aromatic substance for a time ranging from a few hours to as much as a week depending on the concentration and other properties of the aromatic substance. The scent bar 40 may be constructed of suitable materials such as poly-olefin plastics which can absorb the aromatic substance and retain up to 30% of the aroma.

In use, the scent bar 40 is soaked in an aromatic substance for an appropriate period of time and inserted into the holster cavity 30 of the base 20. The assembled nasal clip 10 is then positioned so that the free ends 28 of the base engage and grip the septum 4 of the user's nose 2. The proximal edge 22 of the base 20 thus surrounds a portion of the septum 4, and the scent of the aromatic substance diffuses directly to the nasal passages 6 of the user through the openings 32 and 34, while the scent bar 30 remains safely spaced from contact with the user's septum 4.

The nasal clip 10 is primarily for people with heightened sense of smell and nausea due to various conditions. The clip 10 provides a unique aroma therapy usage. Instead of diffusing the aroma into the air and affecting everyone in the vicinity, it effuses the aroma directly into the person's nasal passages 6, therefor making the experience personal. It can be used inconspicuously since it is virtually unseen. It can also be used on the go, whereas the other aroma therapy devices cannot.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. A nasal clip for attachment to a nasal septum of a user, comprising:
    a U-shaped base having a pair of free ends disposed to grippingly engage the nasal septum, the base having a holster cavity in a portion of the base remote from the free ends;
    a scent bar disposed to be received in the holster cavity and secured to the base, wherein the scent bar carries an aromatic substance being inhalable through the user's nasal passages during breathing when the nasal clip is worn, the scent bar being further disposed so that the scent from the aromatic substance when leaving the scent bar is directed towards the user's nasal passages when the nasal clip is worn; and
    wherein the base further comprises separation means to prevent the scent bar from touching generally the nasal septum.

2. The nasal clip of claim 1 further including an opening formed in the base extending from the holster cavity through the base, whereby scent of the aromatic substance diffuses directly toward the user's nasal passages.

3. The nasal clip of claim 2 wherein a plurality of openings are formed in the base extending from the holster cavity through the base.

4. The nasal clip of claim 1 wherein the scent bar is frictionally secured in the holster cavity.

5. The nasal clip of claim 1 wherein the scent bar is formed of a porous material having the aromatic substance absorbed thereon.

6. The nasal clip of claim 5 wherein the porous material is a poly-olefin plastic.

7. The nasal clip of claim 1 wherein the aromatic substance is selected from a group consisting of essential oils and aromatic medications.

8. A nasal clip for attachment to a nasal septum of a user, comprising:
    a U-shaped base having a proximal edge and a distal edge, and having a pair of free ends disposed to grippingly engage the nasal septum, the base having a cavity in a portion of the base remote from the proximal edge;
    a scent bar disposed to be received in the cavity and secured to the base, wherein the scent bar carries an aromatic substance being inhalable through the user's nasal passages during breathing when the nasal clip is worn, the scent bar being further disposed so that the scent from the aromatic substance when leaving the scent bar is directed towards the user's nasal passages when the nasal clip is worn; and
    wherein the base further comprises separation means to prevent the scent bar from touching generally the nasal septum.

9. The nasal clip of claim 8 further including an opening formed in the base extending from the cavity through the base, whereby scent of the aromatic substance diffuses directly toward the user's nasal passages.

10. The nasal clip of claim 9 wherein a plurality of openings are formed in the base extending from the cavity through the base.

11. The nasal clip of claim 8 wherein the scent bar is frictionally secured in the cavity.

12. The nasal clip of claim 8 wherein the scent bar is formed of a porous material having the aromatic substance absorbed thereon.

13. The nasal clip of claim 12 wherein the porous material is a poly-olefin plastic.

14. The nasal clip of claim 8 wherein the aromatic substance is selected from a group consisting of essential oils and aromatic medications.

* * * * *